(12) United States Patent
Hamelin et al.

(10) Patent No.: US 7,951,564 B2
(45) Date of Patent: May 31, 2011

(54) PRIMERS FOR AMPLIFYING MONONUCLEOTIDE SATELLITE MARKERS

(75) Inventors: Richard Hamelin, Paris (FR); Nirosha Suraweera, High Wycombe (GB)

(73) Assignee: Institut National de la Sante et de la Recherche, Paris (FR)

( * ) Notice: Subject to any disclaimer, the term of this patent is extended or adjusted under 35 U.S.C. 154(b) by 0 days.

(21) Appl. No.: 12/385,086

(22) Filed: Mar. 30, 2009

(65) Prior Publication Data

US 2009/0317815 A1 Dec. 24, 2009

Related U.S. Application Data

(62) Division of application No. 10/505,725, filed as application No. PCT/EP03/02654 on Feb. 26, 2003, now Pat. No. 7,521,180.

(30) Foreign Application Priority Data

Feb. 28, 2002 (EP) .................................... 02290483

(51) Int. Cl.
C12P 19/34 (2006.01)
C07H 21/04 (2006.01)
(52) U.S. Cl. ..................................... 435/91.2; 536/24.33
(58) Field of Classification Search .................... None
See application file for complete search history.

(56) References Cited

U.S. PATENT DOCUMENTS 6,150,100 A 11/2000 Ruschoff et al.
7,521,180 B2 * 4/2009 Hamelin et al. ................ 435/6

FOREIGN PATENT DOCUMENTS

WO WO 03/072822 A2 4/2003

OTHER PUBLICATIONS

Suraweera et al., Conservation of mononucleotide repeats within 3' and 5' untranslated regions and their instability in MSI-H colorectal cancer, Oncogene (2001) 20, pp. 7472-7477.*
Buck et al., Design Strategies and Performance of Custom DNA Sequencing Primers, BioTechniques 27:528-536 (Sep. 1999).*
Stratagene, 1988 catalog, p. 39.*
Snabes et al., Preimplantation single-cell analysis of multiple genetic loci by whole-genome amplification, Genetics, Proc. Nati. Acad. Sci. USA, vol. 91, pp. 6181-6185, Jun. 1994.*
Maria Teresa Bassi, et al., "SLC7A8, a Gene Mapping Within the Lysinuric Protein Intolerance Critical Region, Encodes a New Member of the Glycoprotein-Associated Amino Acid Transporter Family", Short Communication, Jun. 14, 1999, pp. 297-303.
C. Richard Boland, et al., "A National Cancer Institute Workshop on Microsatellite Instability for Cancer Detection and Familial Predisposition: Development of International Criteria for the Determination of Microsatellite Instability in Colorectal Cancer", Cancer Research, Nov. 15, 1998, pp. 5248-5257.
Naoyuki Umetani, et al., "Diagnostic Primer Sets for Microsatellite Instability Optimized for a Minimal Amount of Damaged DNA from Colorectal Tissue Samples", Annals of Surgical Oncology, vol. 7, No. 4, 2000, pp. 276-280.
Paivi Peltomaki, "Deficient DNA Mismatch Repair: A Common Etiologic Factor for Colon Cancer", Human Molecular Genetics, vol. 10, No. 7, 2001, pp. 734-740.
Robert Pyatt, et al., "Polymorphic Variation at the BAT-25 and BAT-26 Loci in Individuals of African Origin", Short Communication, American Journal of Pathology, vol. 155, No. 2, Aug. 1999, pp. 349-353.
Xiao-Ping Zhou, et al., "Determination of the Republication Error Phenotype in Human Tumors Without the Requirement for Matching Normal DNA by Analysis of Mononucleotide Repeat Microsatellites", Genese, Chromosomes & Cancer 21:101-107 (1998), pp. 101-107.
Suraweera et al., 2001, Oncogene 20, pp. 7472-7477.
Suraweera et al., 2002, Gastroenterology 123, pp. 1804-1811.
Wong et al., 2006, Carcinogenesis vol. 27, No. 5, pp. 951-955.
Gen Bank (Feb. 6, 2002), cDNA sequence GenBank XM_033393 (also available at http://www.ncbi.nlm.nih.gov/entrez/viewer.fcgi?db=nucleotide&val=14751167), Nos. 3-12 filed in 10 505 725.
GenBank (1991) cDNA sequence GenBank X60152. (also available at: http://www.ncbi.nlm.nih.gov/entrez/viewer.fcgi?db=nucleotide&val=38028).
Loukola et al., 2001, Cancer Research 61, pp. 4545-4549.
Buck et al., 1999, BioTechniques vol. 27, No. 3, pp. 528-536.
Buhard, Oliver et al., Abstract of "Multipopulation Analysis of Polymorphisms in Five Mononucleotide Repeats Used to Determine the Microsatellite Instability Status of Human Tumor," Journal of Clinical Onvology, Original Report, vol. 24, No. 2, pp. 241-251, Jan. 10, 2006.
Dietmaier et al, Technical Advance Multiple Mutation Analysis in Single Tumor Cells with Improved Whole Genome Amplification, American Journal Pathology, vol. 154, No. 1, Jan. 1999, pp. 83-95.

* cited by examiner

Primary Examiner — Mark Staples
(74) Attorney, Agent, or Firm — William E. Beaumont

(57) ABSTRACT

A method for evaluating microsatellite instability associated with a tumour, which entails the steps of amplifying microsatellite loci in a biological sample containing genomic DNA from the tumour and determining sizes of DNA amplification products, wherein at least one microsatellite locus selected from the group consisting of NR 21, NR 22, NR 24 and NR 27, is amplified.

7 Claims, 3 Drawing Sheets

SEQUENCE LISTING

<160> NUMBER OF SEQ ID NOS: 23

<210> SEQ ID NO 1
<211> LENGTH: 1020
<212> TYPE: DNA
<213> ORGANISM: Homo sapiens

<400> SEQUENCE: 1

```
tcccgaaacc agagggatgg ggccggctgt gcagtagaac ggggatcgaa aagaggaaaa      60
caagggcacg aagaccagcg agaaagaaga ggacacctgg gaaaggcgga agcagaagac     120
ggggaaggga aaagaaaccc aaagcaggtg gaaaccagat ctagagcaac accgtcaggt     180
tcacagtttg tttttctaga agagaagaaa gtacctgagg attgctcttt tttcctaccg     240
ttaatgaaaa ctacttttgt cttcatcata aaagaaaaaa ctaaggggag gtaaaggcag     300
tctcctgttt tattaggggg agaggtgaag ggaaatccag gctcactttc tgaataagcc     360
actgcctggt gcacagagca gaaccatcct ggtttctgaa gacacatccc tttcagcaga     420
attccagccg gagtcgctgg cacagttcta tttttatatt taaatgtatg tctcccctgg     480
cctttttttt tttttttttt tttagcaaca cttttcttgt ttgtaaacgc gagtgaccag     540
aaagtgtgaa tgcggagtag gaatattttt cgtgttctct tttatctgct tgccttttt      600 agagagtagc agtggttcct atttcggaaa aggacgttct aattcaaagc tctctcccaa     660
tatatttaca cgaatacgca tttagaaagg gaggcagctt ttgaggttgc aatcctactg     720
agaaggatgg aagaaggagc caggcaccga aacaacaccg aaaagaaaca cccaggtggg     780
ggcgagtcgg acgccagccc cgaggctggt tccggagggg gcggagtagc cctgaagaaa     840
```

-continued

| | |
|---|---|
| gagatcggat tggtcagtgc ctgtggtatc atcgtaggtg agttccattc cttcccgcgg | 900 |
| accccctcctc tccctctgg tggtcctcct gtgagatctt aacccttcga aagcattatt | 960 |
| gttcttccta ttccttagaa aaggattgtc agtcacctga gctgtaactc acctccactg | 1020 |

<210> SEQ ID NO 2
<211> LENGTH: 1020
<212> TYPE: DNA
<213> ORGANISM: Homo sapiens

<400> SEQUENCE: 2

| | |
|---|---|
| agtgcaggaa atagagaaaa agttcacatg tttatattta gctacatttt cttctctctc | 60 |
| tgaagaactt aaggtatata gagtcatata gaaccacata ggagtatatc tctcatataa | 120 |
| gaaaagattg agaacccttg atctatgtgg agggtagatc agtaatattg gtcctcacag | 180 |
| aggtattcca aaaggctaag cagagagaat ctagtctcta gtcagtgctt gtgtattcac | 240 |
| agccctaaac caggctgcag aacccaacat aatcctgccc actctgggtg aatccatttt | 300 |
| agtagaaaat ttctccaaag ttgatctgat tgtaaatatt aaactgacat ctttatgttg | 360 |
| caggtaaagg acctggataa tcgaggcttg tcaaggacat aaatgtcacg tccagctctg | 420 |
| atatgcttcg cactgagcac atcacattta ggacgttgaa gatttttttt tttttttttt | 480 |
| tttaatatgc agtttgtaag aacaaaactg gatggcatca gaattgtctg gaagttttgt | 540 |
| cttgggcagt atgggctggg ccaaatgaaa tgatttttat aattctaaac aggttaccaa | 600 |
| atgaaatgtc atggctttac tttggtcaat taaagggggg aatttttta aaaaatgtgc | 660 |
| cttatttgtt ttgacttata actgatttga gggaggcaaa agctatgcta ggctgccaga | 720 |
| aggacataag cagaccttgt ccattctctt agctccctaa attagccaaa tagagacttc | 780 |
| tttctcaaat caggaaaact atcaaagacc aattcagatc ctacatttac agacagtttt | 840 |
| gtcataaccc tttgcattgc agcacctagt acaattcctt ggaaacagcg tggctcaata | 900 |
| aatttttatt gaatgaataa atgtgggacc agaagagtgc tagaagagtg cctttctggg | 960 |
| ctactatgtc tctgttctca atgtcttta tccttagacg ctctttgact ttataaatca | 1020 |

<210> SEQ ID NO 3
<211> LENGTH: 960
<212> TYPE: DNA
<213> ORGANISM: Homo sapiens

<400> SEQUENCE: 3

| | |
|---|---|
| gtgctaagct gtggtacagt aacaagcccg cagagagcta tgtctccctt aaaacctgac | 60 |
| gggaaccatt ctgtcttatt ctatcctcat tatttggaac atctggcttc caaagtcacc | 120 |
| acaagggcgg aagagaaagc tagaggaatt tgtaggatat tttcttagac ccaggcttac | 180 |
| atcacttctg tccacatcta ataagccaga acccagcacc tagaagctag gaaagtaaac | 240 |
| aagcacctcg aaagttggtt aataccaaga acctctctca cagttatatt ttgcatacta | 300 |
| ctgttaagcc agtctttgca aatgacccct tcctgcccat cactgccttc ctcaagacct | 360 |
| aaaatagctc cctatttagt gaaaaattat ctgaatattt aaggtctgcc ttaacgtgat | 420 |
| ccccattgct gaattttacc tcctgactcc aaaaactctt ctcttccctg ggcccagtcc | 480 |
| tatttttttt tttttttttt tttttgtgag acagagtctc actctgtcac ccaggttgga | 540 |
| atgcaatggc acaatctccg ctcactgcaa gctccgcctc cgggttcac gccattctcc | 600 |
| tgcctcagcc tcccgaatag ctgggactac aggtgcccgc caacacgccc ggctaatttt | 660 |
| ttgtattttt agtagagacg gggtttcacc gtgttagcca ggatggtctc aatctcctga | 720 |

```
cctcgtgatc cgcccgcctc ggcctcccaa agtgctggga ttacagacgt aagtcaccgt    780
gcccggccta tatttttatt ttattaaagg ttaggcacta gatgaccttg actctaggca    840
tctgcattct cttgatcttt gcttagggtg aagctcagaa aaggacttgg ttctgaaagg    900
ctgtctggaa ttagattgtc ctacgtgatt cccagtgaat tgagatgaat ttcctctgga    960

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
taaatgtatg tctcccctgg                                                  20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
attcctactc cgcattcaca                                                  20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaggcttgtc aaggacataa                                                  20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aattcggatg ccatccagtt                                                  20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccattgctga attttacctc                                                  20

<210> SEQ ID NO 9
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 9
attgtgccat tgcattccaa                                                  20

<210> SEQ ID NO 10
<211> LENGTH: 1020
<212> TYPE: DNA
<213> ORGANISM: Homo sapiens

<400> SEQUENCE: 10
ccgcctcgtc ctcccggagt gcttggatta cagcatgagc cactgcgccc ggcccccatt      60
ttagttttga tggacatttg ggtaattttc ttttttggct attctaaata atgctgcaat     120
tactgttaat tttcaccttg taaaaaccat tttcaaatct caagagatta accttagtt     180 ttcttggttt ggattgggaa ggaacaccaa ggaaaatgag ggacttcaga atttattttc     240
attttgcatt tgttttttaa aatctttaga actggatcca gtggtataga aatcttcgat     300
ttttaaattc ttaattttag gttgcagttt catcactgtc tgcggtaatc aagttttttag    360 aactcttatc agatgattcc aactttggac agtttgaact gactacttttt gacttcagcc    420 agtatatgaa attggatatt gcagcagtca gagcccttaa cctttttcag gtaaaaaaaa    480 aaaaaaaaa aaaaaaaag ggttaaaaat gttgaatggt taaaaatgt tttcattgac       540 atatactgaa gaagcttata aaggagctaa atatttga aatattatta tacttggatt       600
agataactag ctttaaatgg ctgtatttt ctctcccctc ctccactcca cttttttaact    660 ttttttttt taagtcagag tctcacttgt tccctaggcc agagtgcagt ggcacaatct     720
cagcccactc taacctccac ctcccaagta gttgggatta cagttgcctg ccaccatgcc    780
tggttaattt ttatatttt agtagggttg cggggacagg gtttcaccat gttggccagg    840
ttggtctcaa acttctgacc ttaggtgatc ctcccacctc ggcttccaa agtgctggga    900 ttacaggctt gagccatcgt gcccagccta ctttttactt ttttagagac tgggcttggt    960
ggagtgaagt ggcaagatca tagctcactg cagtattgaa ctcctgggct caagcgatct   1020

<210> SEQ ID NO 11
<211> LENGTH: 1080
<212> TYPE: DNA
<213> ORGANISM: Homo sapiens

<400> SEQUENCE: 11
cattcccagt agcaatgatg cagaccagtt ctgctttatg gtagcagtgc caatggtcaa     60
tggcagttag ggttgcaagt gggtgtttgg ggtcagagca tatgttttttg tgcctgagta   120 tctttctata gatatgggat ctttgcttta attcgccatc cctctcctct atggattttg    180
taacccagcc taggattgtt aaatattaac tttgtgattc agcatctacc tttcctggac    240
accagggaag tgatctgcct gcaagttcac attagttcat tcattaccag cctttggtat    300
gtcattgcca ctgtcttttc ctttcctgac ctttatggtt gtaattgcta agaaaaatcc    360
tctcttcctc acaggctcat acatagaaag agatgtgact cccgccatca tggaggatga    420
cgagttggcc ctagcttag aagacttgct gagcttttct taccaggtgg caagggcat     480 ggctttcctc gcctccaaga atgtaagtgg gagtgattcc ctaaagagtt ttgtgttttg    540 ttttttgat ttttttttt tttttttt tttgagaaca gagcatttta gagccatagt       600
taaaatgcag aatgtcattt tgaagtgtgg taaccaaaag cagaggaaat ttagtttctt    660
catgttccaa ctgctgtctc tttggaattc ctgttctaat ttataagctg taaagtacaa   720

```
gcctgtctaa atgagttttt ctatgaatat tcttttatat gcagtgaaat tcttttaaaa    780
cttttggctt ttaggatata ggatatgttc ctagagaaca gaatcatttt atcagtaaaa    840
gcagagggca cctcatagtt acaaggcttg gggtgaagca tagacttgag ttttattgaa    900
gttagatcca aatattatat gtgtggctta tgaagtgtca ggaaataagg ggtcagaggg    960
agtaataaac acttgggaga aggttaggaa tggaaagaat gatggaacca aaacaaggag   1020
catggtctgt ggaagggtga aaggagttcc ttaggaagta agattaaccg aacagaatga   1080
```

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tcgcctccaa gaatgtaagt                                                  20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tctgcatttt aactatggct c                                                21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgactacttt tgacttcagc c                                                21

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aaccattcaa catttttaac cc                                               22

<210> SEQ ID NO 16
<211> LENGTH: 1020
<212> TYPE: DNA
<213> ORGANISM: Homo sapiens

<400> SEQUENCE: 16

```
cttctacagt gacaaagaaa aatcaagaac aaagcttttt gatatgtgca acaaatttag     60
aggaagtaaa aagataaatg tgatgattgg tcaagaaatt atccagttat ttacaaggcc    120
actgatattt taaacgtcca aaagtttgtt taaatgggct gttaccgctg agaatgatga    180
ggatgagaat gatggttgaa ggttacattt taggaaatga agaaacttag aaaattaata    240
```

-continued

```
taaagacagt gatgaataca aagaagattt ttataacaat gtgtaaaatt tttggccagg    300
gaaaggaata ttgaagttag atacaattac ttacctttga gggaaataat tgttggtaat    360
gagatgtgat gtttctcctg ccacctggaa acaaagcatt gaagtctgca gttgaaaagc    420
ccaacgtctg tgagatccag gaaaccatgc ttgcaaacca ctggtaaaaa aaaaaaaaaa    480
aaaaaaaaaa agccacagtg acttgcttat tggtcattgc tagtattatc gactcagaac    540
ctctttacta atggctagta aatcataatt gagaaattct gaattttgac aaggtctctg    600
ctgttgaaat ggtaaattta ttattttttt tgtcatgata aattctggtt caaggtatgc    660
tatccatgaa ataatttctg accaaaacta aattgatgca atttgattat ccatcttagc    720
ctacagatgg catctggtaa cttttgactg ttttaaaaaa taaatccact atcagagtag    780
atttgatgtt ggcttcagaa acatttagaa aaacaaaagt tcaaaatgt tttcaggagg     840 tgataagttg aataactcta caatgttagt tctttgaggg ggacaaaaaa tttaaaatct    900
ttgaaaggtc ttattttaca gccatatcta aattatctta agaaaatttt taacaaaggg    960
aatgaaatat atatcatgat tctgtttttc caaaagtaac ctgaatatag caatgaagtt    1020
```

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gagtcgctgg cacagttcta    20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctggtcactc gcgtttacaa    20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gctgaatttt acctcctgac    20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aaccatgctt gcaaaccact    20

```
<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgataatact agcaatgacc                                                   20

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
taccaggtgg caaagggca                                                    19

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ctgcggtaat caagttttta g                                                 21
```

PRIMERS FOR AMPLIFYING MONONUCLEOTIDE SATELLITE MARKERS

The present application is a division of application Ser. No. 10/505,725, filed Jun. 13, 2005, which has issued as U.S. Pat. No. 7,521,180, which is a 371 of PCT/EP2003/002654, filed on Feb. 26, 2003, the latter of which claims priority to EP 02290483.3, filed on Feb. 28, 2002.

FIELD OF THE INVENTION

The invention concerns new microsatellite markers and their use for the detection of the microsatellite instability (MSI) associated with some tumours.

BACKGROUND OF THE INVENTION

Microsatellites are short DNA motifs (1-10 base pairs), which occur as tandem repeats at numerous loci throughout the genome.

The microsatellite instability (MSI) phenotype is defined as the presence in tumour DNA of alternative sized microsatellites that are not seen in the corresponding germline DNA (AALTONEN et al., Science, 260(5109), 812-816, 1993; IONOV et al., Nature, 363(6429), 558-561, 1993; THIBODEAU et al., Science, 260(5109), 816-819, 1993; IACOPETTA et al., Hum. Mutat., 12(5), 355-360, 1998).

The MSI phenotype is a characteristic of the hereditary non-polyposis colorectal cancer (HNPCC) syndrome, wherein it can be detected in more than 90% of all HNPCC tumours (LIU et al., Nature Med., 2, 169-174, 1996); it also occurs in approximately 15% of sporadic colon and gastric tumours. It has also been detected in other tumours, such as pancreatic carcinomas (HAN et al., Cancer Res., 53, 5087-5089, 1993), prostate carcinomas (GAO et al., Oncogene, 9, 2999-3003, 1994), carcinomas of the endometrium (RISINGER et al., Cancer Res., 53, 5100-5103, 1993; PELTOMAKI et al., Cancer Res., 53, 5853-5855, 1993).

MSI reflects an underlying mismatch repair (MMR) defect that fails to recognize errors introduced during the replication of microsatellite sequences. In the familial cancer syndrome HNPCC, the MSI phenotype is caused by germline mutations in the mismatch repair (MMR) genes hMSH2, HMLH1 and less frequently in hPMS1, hPMS2 and hMSH6 (KINZLER et al., Cell, 87, 159-170, 1996). In sporadic cancers it is often caused by methylation of the hMLH1 promoter leading to the transcriptional silencing of this gene (HERMAN et al., Proc. Natl. Acad. Sci. USA, 95(12), 6870-6875, 1998).

MSI colonic and gastric tumours have distinctive molecular and clinicopathological profiles and are often associated with favourable prognosis (LOTHE et al., Cancer Res., 53, 5849-5852, 1993; KIM et al., Am. J. Pathol., 145, 148-156, 1994; OLIVEIRA et al., Am. J. Pathol., 153, 1211-1219, 1998). There is also evidence to suggest that colorectal cancer patients with MSI tumours show good survival benefit from 5FU-based chemotherapy (ELSALEH et al., The Lancet, 355, 1745-1750, 2000; LIANG et al., Int. J. Cancer, 101, 519-525, 2002) and therefore MSI might be a useful molecular predictive marker for response to this type of adjuvant therapy. Routine analysis of MSI status also has clinical application for assisting in the diagnosis of suspected HNPCC cases (AALTONEN et al., N. Eng. J. Med., 338, 1481-1487, 1998). Indeed, tumours from HNPCC patients lack phenotypic features that readily distinguish them from sporadic tumours and hence the diagnosis of this disease was historically based on family history of cancer using for example the Amsterdam criteria (VASEN et al., Dis. Colon Rectum, 34, 424-425, 1991; VASEN et al., Gastroenterology, 115, 1453-1456, 1999). Such criteria are too restrictive however and identify only a fraction of HNPCC families so that the true incidence of this disease is not known and estimates vary from 0.5 to 13%. Given that familial carriers of MMR defects have a greater than 80% risk of developing cancer, it is important to devise efficient and cost-effective ways to detect this condition. For this purpose, molecular-based laboratory approaches are now being developed that may help in establishing HNPCC diagnosis. Two methods are generally proposed: microsatellite genotyping and immunohistochemistry of the main mismatch repair proteins. The use of one or the other, or both of these methods is still a matter of debate, based on their relative efficiency, specificity and cost (LINDOR et al., J. Clin. Oncol., 20, 1043-1048, 2002; WAHLBERG et al., Cancer Res., 62, 3485-3492, 2002; TERDIMAN et al., Gastroenterology, 120, 21-30, 2001; LOUKOLA et al., Cancer Res., 61, 4545-4549, 2001). It appears so far that microsatellite genotyping has a higher sensitivity than IHC, but is more expensive and more difficult to set up in routine laboratories. It is thus important to develop simple and accurate methods to determine MSI tumours for predisposition and prognostic diagnosis informations.

Numerous different microsatellites have been studied by investigators with the aim of identifying MSI tumours.

Depending on the type and number of microsatellites analysed, widely variable results for the frequency of MSI in different tumour types have been published (PERUCHO, Cancer Res., 59(1), 249-256, 1999).

The use of a BAT-25 and BAT-26 marker combination has been proposed for the detection of MSI (ZHOU et al., Genes, Chromosomes & Cancer, 21(2), 101-107, 1998; HOANG et al., Cancer Res., 57(2), 300-303, 1997).

The BAT-25 and BAT-26 are mononucleotide repeats respectively located in intron 16 of c-kit and intron 5 of hMSH2. These two repeats are quasimonomorphic in Caucasian populations (HOANG et al., Cancer Res., 57(2), 300-303, 1997; ZHOU et al., Oncogene, 15(14), 1713-1718, 1997). This property allows ready classification of the large allelic size variations seen in MSI tumour DNA as being due to somatic alteration. In the large majority of tumours, analysis of BAT-25 and BAT-26 is sufficient to establish their MSI status without reference to the germline DNA (ZHOU et al., Genes, Chromosomes & Cancer, 21(2), 101-107, 1998).

However, alternative sized BAT-25 and BAT-26 alleles have been identified in 18.4 and 12.6%, respectively, of African Americans (PYATT et al., Am. J. Pathol., 155(2), 349-353, 1999; SAMOWITZ et al., Am. J. Pathol., 154(6), 1637-1641, 1999). Thus, analysis of additional repeats may be needed in order to avoid the occasional false positive result arising from these germline polymorphisms.

Accordingly it has been proposed to complete the analysis of these mononucleotide repeats by an additional analysis of dinucleotide repeats in both the tumour and germline DNA.

For instance, U.S. Pat. No. 6,150,100 proposes the use of 2 mononucleotide repeats selected from BAT25, BAT26 and BAT40, associated with 2 or 3 dinucleotide repeats selected from APC, Mfd15, D2S123, and D18S69, and optionally with the pentanucleotide repeat TP53Alu. Preferred combinations of microsatellite markers disclosed in U.S. Pat. No. 6,150,100 are BAT25, BAT26, APC, Mfd15 and D2S123 or BAT26, BAT40, APC, Mfd15 and D2S123.

In 1997 an international consensus meeting on the detection of MSI recommended a panel of five markers for the uniform analysis of MSI status (BOLAND et al., Cancer Res., 58(22), 5248-5257, 1998). This included two mononucleotide (BAT-25 and BAT-26) and three dinucleotide (D5S346, D2S123 and D17S250) repeats. Tumours with instability at two or more of these markers were defined as being MSI-H. Tumours with instability at one marker, and without instability were defined as MSI-L and MSS respectively. MSI-H cancers have distinct clinicopathological features from MSI-L and MSS tumours.

Some of the characteristics of dinucleotide repeats make their use as markers of the MSI status somewhat problematical. The dinucleotide repeats in the above panels generally show instability in only 60-80% of MSI-H tumours (SUTTER et al., Mol. Cell Probes, 13(2), 157-165, 1999). There is some evidence to suggest that loss of MMR and subsequent alteration of mononucleotide repeats occurs earlier in the MSI-H tumour progression pathway than the mutation of dinucleotide repeats (PERUCHO et al., Cold Spring Harb. Symp. Quant. Biol., 59, 339-348, 1994). Furthermore, some MSI cell lines with MMR deficiency caused by hMSH6 mutation do not show alteration in dinucleotide repeats (AKIYAMA et al., Cancer Res., 57(18), 3920-3923, 1997). Therefore the underlying MMR deficiency affecting mononucleotide and dinucleotide repeats may be different and the analysis of both may lead to misinterpretation of the MSI status of some tumours. In many instances the analysis of dinucleotide repeats adds no further information to the results obtained by analysis of mononucleotide repeats (DIETMAIER et al., Cancer Res., 57(21), 4749-4756, 1997; LOUKOLA et al., Cancer Res., 61(11), 4545-4549, 2001).

In addition, unlike mononucleotide repeats such as BAT-25 and BAT-26, dinucleotide repeats are highly polymorphic. Therefore, their use for the identification of MSI in tumour DNA always requires the analysis of corresponding germline DNA.

This makes the MSI screening process considerably more time-consuming and expensive, as well as introducing potential errors due to mixing of germline and tumour DNA samples. Moreover, the interpretation of size alterations in these dinucleotide repeats is difficult and can lead to misclassification (PERUCHO, Cancer Res., 59(1), 249-256, 1999). Finally, in many situations germline DNA from cancer patients is not readily available.

For all these reasons, the methods using BAT-26 and BAT-25 either alone, or in combination with dinucleotide repeats are not completely satisfactory for the accurate determination of MSI status in human tumours and there is an urgent need for improvement.

Thus, multiple, quasimonomorphic mononucleotide repeats are needed for the accurate diagnosis of MSI tumours.

SUMMARY OF THE INVENTION

The inventors have now identified new mononucleotide repeats that are conserved in germline DNA from Caucasian and African subjects and that, similar to BAT-25 and BAT-26, are highly sensitive to somatic deletion in MSI-H tumours.

BRIEF DESCRIPTION OF THE DRAWINGS

FIG. 1a shows an example of the fluorescent peaks observed for each marker, in this case representing the most common allele found in germline DNA.

FIG. 1b shows the size of PCR products and corresponding fluorescent labels which were chosen so as to allow simultaneous analysis of normal-sized alleles with the smaller-sized alleles that are typically seen in MSI-H tumours.

FIG. 1c shows that in addition to the smaller alleles, most MSI-H primary tumours also showed normal-sized alleles presumably originating from contaminating non-cancer cells.

DETAILED DESCRIPTION OF THE PREFERRED EMBODIMENTS

Figure 1:
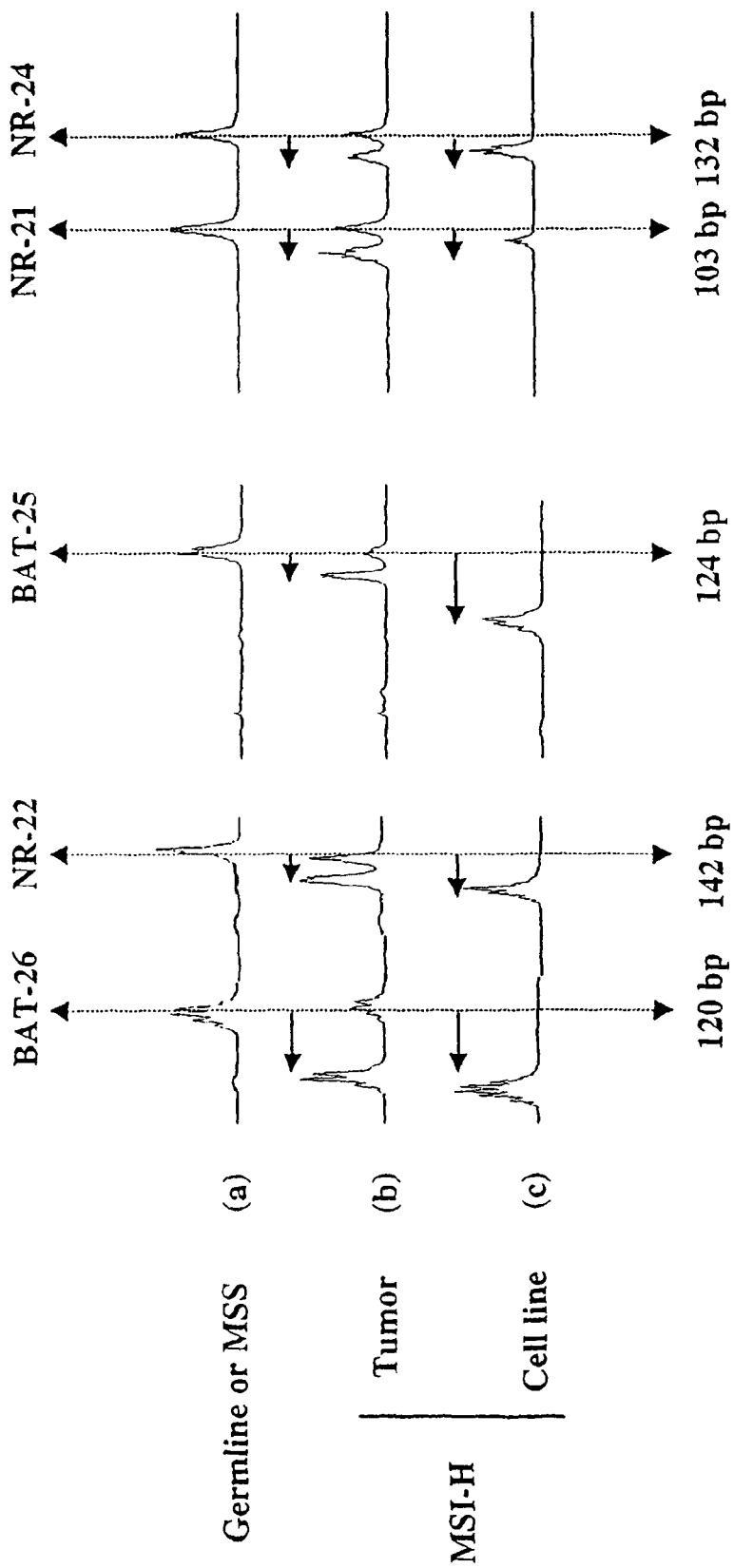
FIG. 1 shows typical allelic profiles of (a) BAT 25, BAT 26, NR 21, NR 22 and NR 24 in DNA from the germline or from MSS tumours, (b) MSI-H primary tumour showing both deleted and normal sized alleles, and (c) MSI-H cell line showing homozygous deletion.

Three of these new microsatellite markers are poly(T) repeats hereinafter referred as NR21, NR22, and NR24.

The NR21 marker is a 21T repeat identified in the 5' untranslated region of the SLC7A8 gene (cDNA sequence GenBank XM_033393).

The NR22 marker is a 22T repeat identified in the 3' untranslated region of the putative trans-membrane precursor protein B5 gene (cDNA sequence GenBank L38961).

The NR24 marker is a 24T repeat identified in the 3' untranslated region of the zinc finger-2 gene (cDNA sequence GenBank X60152).

A fourth microsatellite marker, hereinafter referred as NR27, is a 27A repeat identified in the 5' untranslated region of the inhibitor of apoptosis protein-1 gene (cDNA sequence GenBank AF070674).

The NR21, NR22, NR24 and NR27 markers are useful for the evaluation of microsatellite instability in the diagnosis of tumours.

The invention thus provides a method for evaluating the microsatellite instability associated with a tumour, by amplification of microsatellite loci in a biological sample comprising genomic DNA from said tumour and determination of the sizes of the DNA amplification products, characterized in that said method comprises the amplification of at least one microsatellite locus selected among NR21, NR22, NR24 and NR27.

According to a preferred embodiment of the invention, said method comprises the amplification of the two microsatellite loci NR21 and NR24, and the amplification of a third microsatellite locus selected among NR22 and NR27.

Advantageously, said method further comprises the amplification of at least one microsatellite locus different from NR21, NR22, NR24 and NR27. Preferably, said microsatellite locus is a mononucleotide repeat locus. More preferably this mononucleotide repeat locus is selected among BAT-25 and BAT-26.

According to a particular embodiment, the method of the invention comprises the amplification of the five microsatellite loci BAT-25, BAT-26, NR21, NR22, and NR24.

According to another particular embodiment, the method of the invention comprises the amplification of the five microsatellite loci BAT-25, BAT-26, NR21, NR27 and NR24.

Microsatellite instability at each of these loci is evaluated by comparison of the size of the amplification product obtained from tumoral DNA with the size of the amplification product obtained from normal (i.e. non-tumoral) DNA with the same set of primers.

This comparison can be performed in the conventional way, by obtaining an amplification product from normal DNA from the same subject with the same set of primers, and using it as a reference.

However, the present invention makes it possible, in most of cases, to avoid the need to amplify normal DNA from the same subject. Instead, the comparison can be made by reference to the average size of amplification products obtained from normal DNAs of a pool of subjects with the same set of primers. In these cases, microsatellite instability is assumed in the case of locus BAT-26 if the size of the amplification product obtained from tumoral DNA is shorter of more than 3 bp than the average size of the amplification product obtained from normal DNA using the same set of primers, and in the case of loci BAT-25, NR21, NR22, NR24 and NR27, if the size of the amplification product obtained from tumoral DNA is shorter of more than 2 bp than the average size of the amplification product obtained from normal DNA using the same set of primers.

Tumoral genomic DNA can be obtained from different sources including principally biopsies or tumoral tissues, or body fluids or secretions containing disseminated tumour cells, paraffin embedded tissue.

The invention also provides reagents for carrying out the method of the invention.

In particular, the invention provides pairs of primers suitable for the amplification of a microsatellite locus selected among NR21, NR22, NR24 and NR27.

Suitable primers can be derived from the genomic sequences surrounding said microsatellite loci.

For instance:
primers allowing the amplification of NR21 can be derived from the genomic sequence GenBank AL117258, and preferably from the portion thereof represented by SEQ ID NO: 1;
primers allowing the amplification of NR22 can be derived from the genomic sequence GenBank AP001132, and preferably from the portion thereof represented by SEQ ID NO: 2;
primers allowing the amplification of NR24 can be derived from the genomic sequence GenBank AC092835, and preferably from the portion thereof represented by SEQ ID NO: 3;
primers allowing the amplification of NR27 can be derived from the genomic sequence GenBank AP001167, and preferably from the portion thereof represented by SEQ ID NO: 16.

By way of example:
a pair of primers suitable for the amplification or NR21 consists of the following oligonucleotides:

```
TAAATGTATGTCTCCCCTGG      (SEQ ID NO: 4)
ATTCCTACTCCGCATTCACA      (SEQ ID NO: 5)
``` a pair of primers suitable for the amplification or NR22 consists of the following oligonucleotides:

```
GAGGCTTGTCAAGGACATAA      (SEQ ID NO: 6)
AATTCGGATGCCATCCAGTT      (SEQ ID NO: 7)
``` a pair of primers suitable for the amplification or NR24 consists of the following oligonucleotides:

```
CCATTGCTGAATTTTACCTC      (SEQ ID NO: 8)
ATTGTGCCATTGCATTCCAA.     (SEQ ID NO: 9)
```

The above primers give when used on normal DNA, amplification products of 104, 143, and 134 bp for NR21, NR22 and NR24 respectively.

They can advantageously be labelled with fluorescent dyes and used in multiplex PCR assays. Preferably, different fluorescent dyes will be used for primers that give amplification products of similar size (i.e having sizes differing of less than 15-20 pb). This allows to avoid uncertainties that might result from overlapping of PCR products due to the average deletion of 5-12 bp for these markers in MSI tumors.

If one prefers not to use different fluorescent dyes, primers can be designed in order to give amplification products of clearly distinct size (i.e having sizes differing of at least 15 pb and preferably of at least 20 pb between different markers). This allows a clear separation between markers on a size basis by standard electrophoresis techniques, even when deleted due to microsatellite instability in tumor DNA.

Primers giving amplification products of clearly distinct size for NR21, NR24, and NR27 are by way of example:
a pair of primers suitable for the amplification or NR21 consists of the following oligonucleotides:

```
GAGTCGCTGGCACAGTTCTA;     (SEQ ID NO: 17)
CTGGTCACTCGCGTTTACAA;     (SEQ ID NO: 18)
``` a pair of primers suitable for the amplification or NR24 consists of the following oligonucleotides:

```
GCTGAATTTTACCTCCTGAC;     (SEQ ID NO: 19)
ATTGTGCCATTGCATTCCAA;     (SEQ ID NO: 9)
``` a pair of primers suitable for the amplification or NR27 consists of the following oligonucleotides:

```
AACCATGCTTGCAAACCACT;     (SEQ ID NO: 20)
CGATAATACTAGCAATGACC.     (SEQ ID NO: 21)
```

When used on normal DNA, the above primers give amplification products of 131, 109 and 87 bp for NR24, NR21 and NR27 respectively.

The invention also provides a kit for the analysis of microsatellite instability, characterized in that it comprises at least two pairs of primers suitable for the amplification of at least two microsatellite loci selected among NR21, NR22, NR24, and NR27.

Advantageously said kit comprises at least:
one pair of primers suitable for the amplification of NR21;
one pair of primers suitable for the amplification of NR24;
one pair of primers selected among a pair of primers suitable for the amplification of NR22 and a pair of primers suitable for the amplification of NR27.

According to a preferred embodiment said kit further comprises at least one pair of primers suitable for the amplification of at least one microsatellite locus different from NR21, NR22, NR24 and NR27. Preferably, said microsatellite locus is a mononucleotide repeat locus. More preferably this mononucleotide repeat locus is selected among BAT-25 and BAT-26.

Primers allowing the amplification of BAT-26 can be derived from the genomic sequence GenBank AC0799775, and preferably from the portion thereof represented by SEQ ID NO: 10

Primers allowing the amplification of BAT-25 can be derived from the genomic sequence GenBank AC092545, and preferably from the portion thereof represented by SEQ ID NO: 11

By way of example, a kit of the invention can comprise:
a pair of primers suitable for the amplification of BAT-25, consisting of the following oligonucleotides:

```
TCGCCTCCAAGAATGTAAGT       (SEQ ID NO: 12)
TCTGCATTTTAACTATGGCTC;     (SEQ ID NO: 13)
``` a pair of primers suitable for the amplification of BAT-26, consisting of the following oligonucleotides:

```
TGACTACTTTTGACTTCAGCC      (SEQ ID NO: 14)
AACCATTCAACATTTTTAACCC;    (SEQ ID NO: 15)
```

When used on normal DNA, the above primers amplify a fragment of 121 bp for BAT-26, and 124 bp for BAT-25.

They can be used in particular in a multiplex PCR assay using different fluorescent dyes, for instance in combination with the NR21 primers SEQ ID NO: 4 and 5, the NR22 primers SEQ ID NO: 6 and 7, and the NR24 primers SEQ ID NO: 8 and 9.

If one prefers to obtain amplification products of clearly distinct size for BAT-25 and BAT-26, one can use for instance:
a pair of primers suitable for the amplification or BAT-25 consisting of the following oligonucleotides:

```
TACCAGGTGGCAAAGGGCA;       (SEQ ID NO: 22)
TCTGCATTTTAACTATGGCTC;     (SEQ ID NO: 13)
``` a pair of primers suitable for the amplification or BAT-26, consisting of the following oligonucleotides:

```
CTGCGGTAATCAAGTTTTTAG;     (SEQ ID NO: 23)
AACCATTCAACATTTTTAACCC.    (SEQ ID NO: 15)
```

When used on normal DNA, the above primers give respectively amplification products of 153 and 183 bp for BAT-25 and BAT-26.

They can advantageously be used in combination with NR21 primers (SEQ ID NO: 17 and 18) and/or NR24 primers (SEQ ID NO: 19 and 9) and/or NR27 primers (SEQ ID NO: 20 and 21), allowing a clear separation of the five markers on a size basis.

Optionally, the kits of the invention can further comprise appropriate reagents and materials useful to carry out DNA amplification.

The method, reagents and kits of the invention can be used in the same applications as the prior art methods of evaluation of microsatellite instability. This includes mainly the diagnosis of the MSI phenotype of tumours, in particular tumours of the gastrointestinal tract, and more specifically colorectal or gastric tumours, or tumours of the endometrium. Tumours with instability at three or more of the BAT-25, BAT-26, NR21, NR22 (or NR27), or NR24 loci are defined as being MSI-H.

The method of the invention has the advantage over the prior art methods of allowing to establish the MSI status without ambiguity in particular in the case of tumours of the gastrointestinal tract, without needing a simultaneous analysis of corresponding germline DNA from each patient.

We propose that concurrent use of these mononucleotide markers in a single pentaplex PCR system allows accurate evaluation of tumour MSI status with 100% sensitivity, 100% specificity. This assay is simpler to use than those involving dinucleotide markers, and is more specific than using BAT-25 and BAT-26 alone. This test could be routinely used in the hospital to provide information on prognosis, as a possible predictor of response to adjuvant therapies, and for the detection of new HNPCC family members.

The invention will be further illustrated by the additional description which follows, which refers to an example of use of the mononucleotide markers of the invention in multiplex PCR analysis. It should be understood however that this example is given only by way of illustration of the invention and does not constitute in any way a limitation thereof.

Example

Material and Methods

Mononucleotide Repeats and Multiplex Polymerase Chain Reaction (PCR)

Three new poly(T) repeats and one new poly(A) repeat were identified respectively in the 3' or 5' untranslated regions of the SLC7A8 (NR21, 21T), trans-membrane precursor protein B5 (NR22, 22T), zinc finger-2 (NR24, 24T), and inhibitor of apoptosis protein-1 (NR27, 27A) genes. Details including primer sequences for these repeats and BAT 25 and BAT 26 are shown in Table I below.

TABLE I

| Name | Gene | GenBank accession (cDNA) | Location of the repeat | Fluorescent marker | colour | Primers | SEQ ID NO | PCR product (bp)* |
|---|---|---|---|---|---|---|---|---|
| BAT 26 | hMSH2 | U04045 | 26(A) intron 5 | FAM$^a$ | blue | TGACTACTTTTGACTTCAGCC | 14 | 121 |
| | | | | | | AACCATTCAACATTTTTAACCC | 15 | |
| | | | | | | CTGCGGTAATCAAGTTTTTAG | 23 | 183 |
| | | | | | | AACCATTCAACATTTTTAACCC | 15 | |
| BAT 25 | c-kit | X06182 | 25(T) intron 16 | NED$^s$ | yellow | TCGCCTCCAAGAATGTAAGT | 12 | 124 |
| | | | | | | TCTGCATTTTAACTATGGCTC | 13 | |
| | | | | | | TACCAGGTGGCAAAGGGCA | 22 | 153 |
| | | | | | | TCTGCATTTTAACTATGGCTC | 13 | |
| NR21 | SLC7A8 | XM_033393 | 21(T) 5'UTR | HEX$^a$ | green | TAAATGTATGTCTCCCCTGG | 4 | 104 |
| | | | | | | ATTCCTACTCCGCATTCACA | 5 | |
| | | | | | | GAGTCGCTGGCACAGTTCTA | 17 | 109 |
| | | | | | | CTGGTCACTCGCGTTTACAA | 18 | |

TABLE I-continued

| Name | Gene | GenBank accession (cDNA) | Location of the repeat | Fluorescent marker | colour | Primers | SEQ ID NO | PCR product (bp)* |
|------|------|--------------------------|------------------------|--------------------|--------|---------|-----------|-------------------|
| NR22 | Putative transmembrane precursor protein B5 | L38961 | 22(T)3'UTR | FAM[a] | blue | GAGGCTTGTCAAGGACATAA<br>AATTCGGATGCCATCCAGTT | 6<br>7 | 143 |
| NR24 | ZINC FINGER 2 (ZNF-2) | X60152 | 24(T)3'UTR | HEX[a] | green | CCATTGCTGAATTTTACCTC<br>ATTGTGCCATTGCATTCCAA<br>GCTGAATTTTACCTCCTGAC<br>ATTGTGCCATTGCATTCCAA | 8<br>9<br>19<br>9 | 134<br><br>131 |
| NR27 | Inhibitor of apoptosis protein-1 | AF070674 | 27(A)5'UTR | | | AACCATGCTTGCAAACCACT<br>CGATAATACTAGCAATGACC | 20<br>21 | 87 |

[s]sense primer
[a]anti-sense primer
*theorical size deduced from GenBank sequence Primers were designed to allow different PCR product sizes to be resolved on 5% denaturing gels run in an ABI PRISM 377 automated DNA sequencer. GENESCAN software (GENOTYPER 2.1) was used to calculate the size, height and area of each fluorescent PCR product.

The following primers were used in the experimentations described below:
  BAT 26 primers: SEQ ID NO: 14 and SEQ ID NO: 15;
  BAT 25 primers: SEQ ID NO: 12 and SEQ ID NO: 13;
  NR21 primers: SEQ ID NO: 4 and SEQ ID NO: 5;
  NR22 primers: SEQ ID NO: 6 and SEQ ID NO: 7;
  NR24 primers: SEQ ID NO: 8 and SEQ ID NO: 9.

One primer in each pair was labelled with one of the fluorescent markers FAM, HEX or NED (PE APPLIED BIOSYSTEMS). The five mononucleotide repeats were amplified in one multiplex PCR containing 20 µM of each primer, 200 µM dNTP, 1.5 mM $MgCl_2$ and 0.75 units of Taq DNA polymerase. The PCR was performed using the following conditions: denaturation at 94° C. for 5 min, 35 cycles of denaturation at 94° C. for 30 sec, annealing at 55° C. for 30 sec and extension at 72° C. for 30 sec, followed by an extension step for 72° C. for 7 min.

DNA Samples

Germline DNA was obtained from 128 Caucasian individuals at the Centre d'Etudes du Polymorphisme Humain (CEPH) in Paris and from 56 individuals of African descent.

A total of 124 colon, 50 gastric tumours, 20 endometrial tumours and 16 colon cell lines that had previously been tested for MSI using several dinucleotide markers and BAT-25 and BAT-26 mononucleotide markers (147 cases) or BAT26 and BAT25 alone (63 cases) (HOANG et al. Cancer Res., 57(2), 300-303, 1997; SERUCA et al., Int. J. Cancer, 64, 32-36, 1995; TIBELETTI et al., Gynecol. Oncol., 73(2), 247-252, 1999). Of these a total of 81 primary colon tumours, 42 primary gastric cancers, 20 primary endometrial tumours and 5 colon tumour cell lines were considered to be MSI-H based on deletions in the above repeats.

Results

Fluorescent Multiplex PCR

The five mononucleotide markers BAT-25, BAT-26, NR21, NR22 and NR24 were co-amplified in a single multiplex PCR mix using the PCR conditions described above, and analysed for size in an automated DNA sequencer. In these conditions, no non-specific bands within the 100-142 bp size range were observed, thus allowing accurate identification of the five markers.

FIG. 1 shows typical allelic profiles of (a), BAT25, BAT26, NR21, NR22 and NR24 in DNA from the germline or from MSS tumours, (b) MSI-H primary tumour showing both deleted and normal sized alleles, and (c) MSI-H cell line showing homozygous deletions.

FIG. 1a shows an example of the fluorescent peaks observed for each marker, in this case representing the most common allele size found in germline DNA.

The size of PCR products and the corresponding fluorescent labels were chosen so as to allow simultaneous analysis of normal sized alleles with the smaller sized alleles containing deletions that are typically seen in MSI-H tumours (FIG. 1b). In addition to the smaller alleles most MSI-H primary tumours also showed normal sized alleles that presumably originate from contaminating non-cancer cells. These were absent in the homozygous mutant MSI-H cell line shown in FIG. 1c.

Figure 2:
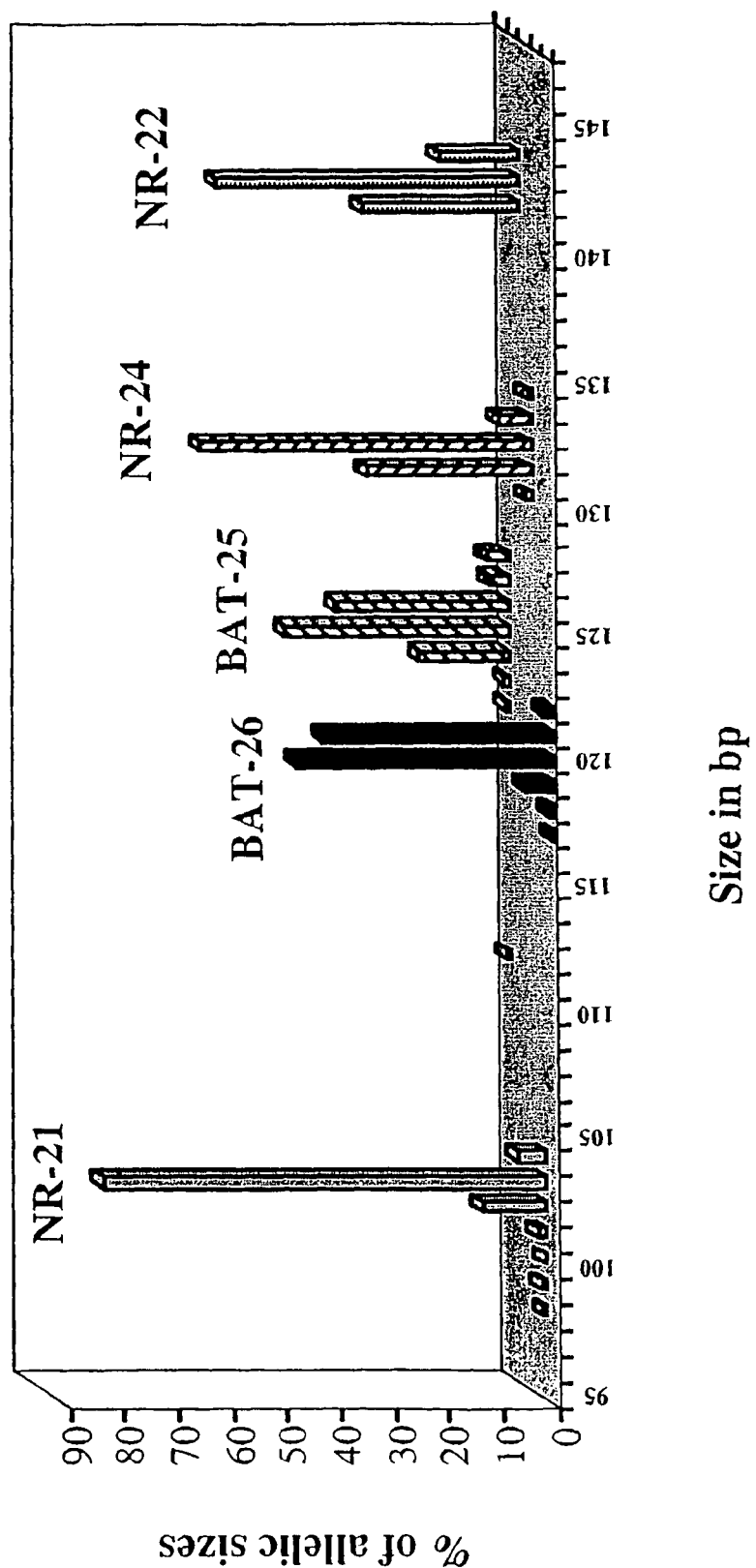
FIG. 2 shows that none of the germline DNA samples tested were polymorphic in more than 2/5 markers.

The most common allelic sizes for BAT-25, BAT-26, NR21, NR22 and NR24 were 124, 120, 103, 142 and 132 bp respectively, although for each repeat, a slight variation in the position of the peaks representing the size of the PCR product was observed (FIG. 2).

Legend of FIG. 2:
  ◪=BAT-25
  ■=BAT-26
  ◫=NR21
  ☒=NR22
  ◼=NR24

In order to account for these variations, for BAT-25, NR21, NR22 and NR24 alleles of ≧3 pb and for BAT-26 allelic sizes of ≧4 pb were considered to be polymorphisms or somatic alterations.

Polymorphisms in Germline DNA

As shown in Table IIa below, each marker was at least 95% monomorphic in 128 germline DNA samples from unrelated Caucasians (CEPH samples).

TABLE IIa

|  |  | BAT-26 | BAT-25 | NR21 | NR22 | NR24 |
|---|---|---|---|---|---|---|
| germline Caucasian | germline DNA | 128/128 (100%) | 126/128 (98.4%) | 122/128 (95.3%) | 128/128 (100%) | 128/128 (100%) |
| germline African | germline DNA | 51/56 (91.1%) | 44/56 (78.6%) | 54/56 (96.1%) | 56/56 (100%) | 52/56 (92.9%) |

Figure 3:
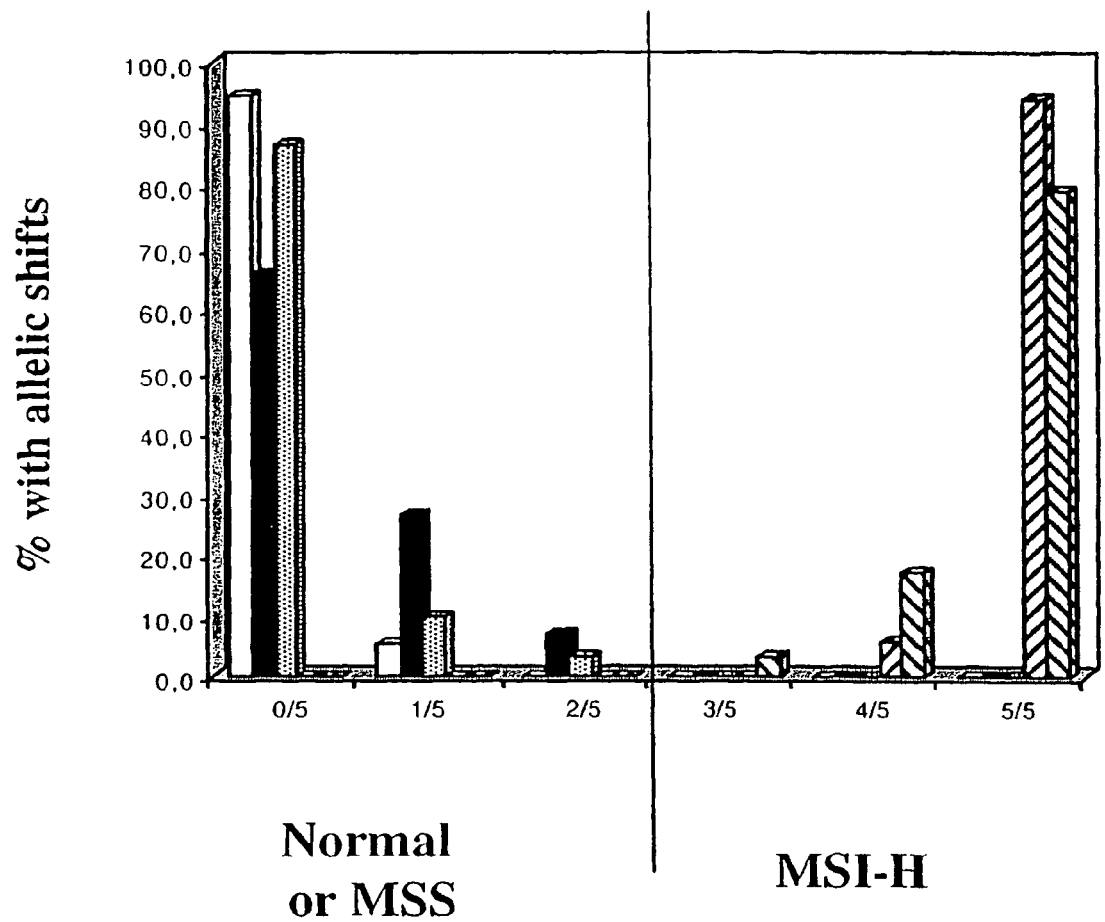
FIG. 3 shows that a total of 104 colon and gastric tumours and cell lines which were previously identified as MSI-H showed amplification data for all five markers. Tumours showed deletions in either all (88 tumours) or 4/5 (9 tumours) mononucleotide repeats.

Furthermore, 121 (94.5%) of this population was monomorphic in all five repeats and the remaining 7 individuals (5.5%) were monomorphic in 4/5 markers. No CEPH DNA sample contained a polymorphism in more than 1 of the 5 repeats. Polymorphisms were more common in African germline DNA, with BAT 25 having the highest level of polymorphism at 21.4%. Although interestingly, of 56 African germline DNA samples tested, 37 (66.1%) were monomorphic in all five repeats, 15 (26.8%) showed a polymorphism in 1/5 markers and 4 (7.1%) in 2/5 markers. None of the germline DNA samples were polymorphic in >2/5 markers. These data are also shown in FIG. 3.

Identification of MSI-H Tumours

Using the above criteria the average deletion observed for each mononucleotide repeat was calculated in MSI-H gastric and colon tumours. The sensitivity, specificity and the average deletions of the five markers in different types of DNA are shown in Table IIb below.

TABLE II

|  |  | BAT-26 | BAT-25 | NR21 | NR22 | NR24 |
|---|---|---|---|---|---|---|
| Colon | average deletion | 11.9 | 7.3 | 6.8 | 5.1 | 5.6 |
|  | MSI-H (sensitivity) | 77/77 (100%) | 72/72 (100%) | 78/78 (100%) | 77/79 (97.5%) | 72/75 (96%) |
|  | MSS (specificity) | 42/43 (97.7%) | 44/44 (100%) | 43/44 (97.7%) | 45/45 (100%) | 43/44 (97.7%) |
| Colon Cell Line | average deletion | 11 | 7.8 | 7.4 | 4.4 | 7.6 |
|  | MSI-H (sensitivity) | 4/4 (100%) | 5/5 (100%) | 5/5 (100%) | 5/5 (100%) | 5/5 (100%) |
|  | MSS (specificity) | 11/11 (100%) | 11/11 (100%) | 11/11 (100%) | 11/11 (100%) | 10/10 (100%) |
| Gastric | average deletion | 12 | 7.2 | 6.8 | 4.9 | 5 |
|  | MSI-H (sensitivity) | 39/39 (100%) | 39/39 (100%) | 37/39 (94.9%) | 38/39 (97.4%) | 26/30 (86.7%) |
|  | MSS (specificity) | 8/11 (72.7%) | 10/11 (90.9%) | 10/10 (100%) | 10/11 (90.9%) | 11/11 (100%) |
| Endometrial | average deletion | 5.9 | 4.6 | 3.9 | 2.9 | 2.4 |
|  | MSI-H (sensitivity) | 15/17 (88.2%) | 18/19 (94.7%) | 17/19 (89.5%) | 14/19 (73.7%) | 10/16 (62.5%) |

For BAT-26, the average deletion was almost 12 bp, or approximately twice the average length of deletion seen with the other markers. Each mononucleotide repeat was deleted in MSI-H tumours with a sensitivity >86%. Allelic shifts due to polymorphisms or somatic mutation were infrequent in non-MSI tumours, resulting in a high degree of specificity for the detection of MSI by each of these markers, with the exception of BAT-26 whose specificity was lowered due to the previous misclassification of 6 tumours as discussed below.

A total of 104 colon and gastric tumours and cell lines which were previously identified as MSI-H showed amplification data for all five markers. Tumours showed deletions in either all (88 tumours) or 4/5 (9 tumours) mononucleotide repeats (FIG. 3). Only one sample showed deletions in 3/5 markers. In 5 cases, previously defined as MSI-H, size alterations were found in only Bat-26 or Bat-25; these samples were considered as misclassified due to ethnic polymorphisms (4 cases) or borderline shortening (1 case). Finally, an additional tumour sample was previously classified as MSI-H using dinucleotide repeats but not BAT-26 (HOANG et al., Cancer Res., 59(1), 300-303, 1997). This sample was monomorphic for all five mononucleotide repeats used in this study, suggesting that it was misclassified with dinucleotide repeats, possibly due to the fact that germline DNA did not match with tumour DNA. In Table II and FIG. 3, these 6 samples were considered as MSS.

Of 55 colon and gastric tumours and cell lines previously classified as MSS and containing data for all 5 repeats, 53 (96.4%) were monomorphic at all 5 markers. One tumour was monomorphic at 4 markers (2%) and 1 tumour was monomorphic at 3/5 (2%) repeats. None of the 55 MSS tumours showed allelic shifts in 3 or more repeats (FIG. 3), still complying with the MSI identification criteria of 2/5 repeat polymorphisms described earlier.

These results are illustrated by FIG. 3, which shows the percentage of samples with allelic size shifts in the five mononucleotide repeats in Caucasian germline DNA (□), African germline DNA (■), MSS tumours (▨), MSI-H colorectal tumours (▨) and MSI-H gastric tumours (◧).

The three mononucleotide repeats NR21, NR22, and NR24 are quasimonomorphic in germline DNA and, similar to BAT-25 and BAT-26, are highly sensitive to somatic deletion in MSI-H tumours. Distinction of MSI-H from MSS tumours is unambiguous when these three new markers are used in conjunction with BAT-25 and BAT-26. Multiplex PCR of these 5 markers has the additional advantage of avoiding the need for simultaneous analysis of corresponding germline DNA from each patient.

Although the quasimonomorphic nature of the three new mononucleotide repeats remains to be fully established in different populations, none of 128 Caucasian and 56 African germline DNA cases had polymorphisms in more than 2 of the repeats. Since all 98 true MSI-H tumours examined here, with successful amplification of the 5 markers, showed deletions in at least 3 markers, the probability of misinterpretation of an MSI result because of polymorphisms in 3 or more of the 5 markers is statistically insignificant. Therefore when the results from all five repeats were analysed together, the MSI status of this entire 159 tumour series was determined unambiguously with 100% sensitivity and specificity. Moreover, this was achieved without the need to analyze corresponding germline DNA.

Table 3 below indicates tumours where polymorphism or borderline deletion on BAT-26 or BAT-25 would have misclassified the MSI status of the corresponding tumour. In all cases, the use of the multiplex panel allowed to unambiguously classify the tumour.

TABLE III

| MSI-H tumours reclassified as MSS with the pentaplex PCR | | | | | |
|---|---|---|---|---|---|
| MSS | BAT-26 | BAT-25 | NR21 | NR22 | NR24 |
| Polymorphisms | 11 | 2 | 0 | 0 | 0 |
|  | 11 | 0 | 0 | 0 | 0 |
|  | 11 | 0 | 0 | 0 | 0 |
|  | 12 | 0 | 0 | 0 | 0 |
| Borderline deletions | 0 | 4 | 0 | 0 | 0 |
| Unstable only in dinucleotide repeats | 0 | 0 | 0 | 0 | 0 |

In a further 31 DNA samples from colon and gastric tumours, only four out of the five markers were correctly amplified. This was probably due to the quality of DNA extracted from formalin-fixed and paraffin-embedded tissues. Twenty four of these cases showed 4/4 or 3/4 unstable loci and were correctly identified as MSI-H, the remaining 7 cases showing 0/4 or 1/4 unstable loci were correctly identified as MSS (results not shown, but included in Table II). Therefore, incomplete amplification of the five repeats could still be used effectively to identify the MSI status of difficult DNA.

We have previously observed that endometrial MSI-H tumours show significant quantitative and qualitative differences in instability compared to gastro-intestinal MSI-H tumours (DUVAL et al., Cancer Res., 62, 1609-1612, 2002). In the present study, 20 endometrial tumours known to be MSI-H were also tested with the same fluorescent pentaplex assay. These tumours showed significantly shorter average lengths of deletions in all five mononucleotide repeats markers compared to MSI-H gastro-intestinal tumours (Table II). Using the MSI detection criteria established with this microsatellite panel, 17/20 endometrial tumours were identified as MSI-H and 1 tumour was identified as MSS (data not shown). It was not possible to conclusively identify the MSI status of the remaining 2 tumours due to the very small allelic shifts observed in all five markers.

Thus, it was possible to effectively identify the MSI status of all 190 colon and gastric tumours and cell lines tested in this experiment, including six samples which were previously misclassified. Because of the smaller size of allelic shifts found in MSI-H endometrial tumours, we recommend the continued analysis of matching germline DNA for routine MSI screening of this cancer type.

Accumulating evidence suggests that MSI status defines a subset of colorectal cancers with distinctive biological and clinical properties, emphasizing the importance of simple and accurate markers for detection. This set of five mononucleotide markers, determines the MSI status of tumours with higher sensitivity and specificity than BAT-25 and BAT-26 alone, and is technically simpler to use than the panel recommended at the Bethesda consensus meeting.

The invention claimed is:

1. A kit, which comprises:
   a) one pair of primers for amplification of NR21, said primers being obtained from SEQ ID NO:1,
   b) one pair of primers for amplification of NR24, said primers being obtained from SEQ ID NO:3, and
   c) one pair of primers for amplifying either NR22 or NR27, said primers being obtained from SEQ ID NO:2 for amplifying NR22, and from SEQ ID NO:16 for amplifying NR27.

2. The kit of claim 1, which further comprises at least one pair of primers selected from the group consisting of:
   a) a pair of primers for amplifying microsatellite locus BAT-25; and
   b) a pair of primers for amplifying microsatellite locus BAT-26.

3. The kit of claim 1, which comprises a pair of primers for amplifying microsatellite locus BAT-25, and a pair of primers for amplifying microsatellite locus BAT-26.

4. The kit of claim 1, which further comprises reagents for DNA amplification.

5. A method for detecting amplified DNA sequences with the kit of claim 1, which comprises detecting said amplified DNA sequences with a different fluorescent dye for each amplified DNA sequence where said amplified sequences differ from each other by less than 20 bp in size.

6. A method for detecting amplified DNA sequences with the kit of claim 1, which comprises detecting said amplified DNA sequences which differ from each other by at least 20 bp in size.

7. The kit of claim 1, which comprises:
   a) one pair of primers for amplification of NR21, said primers being obtained from SEQ ID NO:1;
   b) one pair of primers for amplification of NR24, said primers being obtained from SEQ ID NO:3;
   c) one pair of primers for amplifying NR22, said primers being obtained from SEQ ID NO:2; and
   d) one pair of primers for amplifying NR27 said primers being obtained from SEQ ID NO:16.

* * * * *